(12) United States Patent
Hollmann et al.

(10) Patent No.: US 8,647,848 B2
(45) Date of Patent: Feb. 11, 2014

(54) ENZYMATIC SYNTHESIS OF SPHINGOLIPIDS

(75) Inventors: Frank Hollmann, Den Haag (NL);
Oliver Thum, Ratingen (DE);
Christoph Toelle, Duisburg (DE);
Angelo Provinzano, Bottrop (DE);
Cornelis Gerrit Nijs Korevaar,
Oegstgeest (NL)

(73) Assignee: Evonik Goldschmidt GmbH, Essen (DE)

( * ) Notice: Subject to any disclaimer, the term of this patent is extended or adjusted under 35 U.S.C. 154(b) by 350 days.

(21) Appl. No.: 12/994,008

(22) PCT Filed: May 22, 2009

(86) PCT No.: PCT/EP2009/056206
§ 371 (c)(1),
(2), (4) Date: Nov. 22, 2010

(87) PCT Pub. No.: WO2009/150022
PCT Pub. Date: Dec. 17, 2009

(65) Prior Publication Data
US 2011/0077302 A1     Mar. 31, 2011

(30) Foreign Application Priority Data
Jun. 13, 2008 (DE) .......................... 10 2008 002 409

(51) Int. Cl.
*C12P 13/02* (2006.01)
(52) U.S. Cl.
USPC ........... 435/129; 435/196; 435/197; 435/198; 435/255.2; 435/254.1
(58) Field of Classification Search
USPC ............ 435/129, 196, 197, 198, 255.1, 254.1
See application file for complete search history.

(56) References Cited

U.S. PATENT DOCUMENTS

| 5,023,133 | A | * | 6/1991 | Yodice et al. ................. 428/332 |
| 5,610,040 | A | * | 3/1997 | Smeets et al. ................. 435/129 |
| 2004/0133025 | A1 | * | 7/2004 | Nguyen ........................ 556/427 |
| 2005/0096394 | A1 | * | 5/2005 | Hoorn et al. .................. 514/602 |
| 2009/0181439 | A1 | | 7/2009 | Thum et al. |

FOREIGN PATENT DOCUMENTS

| WO | WO 94/26919 | 11/1994 |
| WO | WO 97/09307 | 3/1997 |
| WO | WO 2006/002909 A2 | 1/2006 |
| WO | WO 2009/150022 A2 | 12/2009 |
| WO | WO 2009/150023 A2 | 12/2009 |

OTHER PUBLICATIONS

Enzyme Nomenclature E.C. Webb, editor (Academic Press, Inc.: San Diego) pp. 306-307.*
Varma et al. Asian J. Biochem. (2007) 2(4): 279-283.*
Yapoidjian et al. Eur. J. Biochem. (2002) 269: 1613-1621.*
Gonzalez-Sabin et al. Tetraheron Assymetry (2002) 13: 1315-1320.*
Uppenberg et al. Biochemistry (1995) 34: 16838-16851.*
Ericsson et al. J. Mol. Biol. (2008) 376: 109-119.*
Takanami, Tsukasa et al., "Chemo-enzymatic short-step total synthesis of symbioramide", Tetrahedron Letters (2005), vol. 46, pp. 3291-3295.

* cited by examiner

*Primary Examiner* — Susan Hanley
(74) *Attorney, Agent, or Firm* — Scully, Scott, Murphy & Presser, P.C.

(57) ABSTRACT

The invention relates to the enzymatic synthesis of sphingolipids and compositions that contain sphingolipids from lysosphingolipids and carbonic esters, and to cosmetic, dermatological or pharmaceutical formulations containing said sphingolipids or compositions.

19 Claims, 5 Drawing Sheets

ENZYMATIC SYNTHESIS OF SPHINGOLIPIDS

FIELD OF THE INVENTION

The invention relates to the enzymatic synthesis of sphingolipids and compositions comprising sphingolipids from lysosphingolipids and carboxylic esters, and to cosmetic, dermatological or pharmaceutical formulations which comprise these sphingolipids or compositions.

PRIOR ART

The invention relates to a process for the biocatalytic preparation of sphingolipids of the general formula I by reacting a lysosphingolipid of the general formula II with a carboxylic ester of the general formula III, where $R^1$, $R^2$, $R^3$ and X are as defined below.

The sphingolipids are used as cosmetic and/or dermatological active components.

Sphingolipids of the general formula I with $R^2$=H are called ceramides and are polar lipids which occur naturally in the skin (stratum corneum). In the outer corneocytes, ceramides represent a major constituent (40-65% of the lipid content) of the cell membranes and thus play a central role in the protective function thereof by, for example, regulating water permeability. With increasing age, keratinocytes lose a large part of their ceramide synthesizing activity and thus the skin loses part of its protective effect and, for example, can no longer completely inhibit epidermal water loss. This can be at least partly compensated by topical application of ceramides Farwick, M. et al., *Int. J. Cosm. Sci.*, 2007, 29(4), 319-329 or Klee, S. K. et al. *Basic Clinic. Dermatol.*, 2007, 40, 155-165).

In addition, positive effects of ceramides have been reported in the treatment of atopic dermatitis (Kerscher, M. et al., *Eur. J. Dermatol.*, 1991, 1, 39-43; Imokawa, G. et al., *J. Soc. Cosmet. Chem.* 1989, 40, 500-507)

In view of the demographic development in many industrialized countries, especially in Germany, there is expected to be a further growth in the demand for ceramides.

In the prior art, ceramides are prepared by Schotten-Baumann-analogous N-acylation of lysosphingolipids of the general formula II with $R^2$=H, such as, for example, phytosphingosine (general formula II with $R^2$=H and X=$CH_2$—HCOH) using activated carboxylic acid derivatives.

The phytosphingosine is typically of fermentative origin.

The activated carboxylic acid is typically the carbonyl chloride which is either employed as such or prepared in situ from the carboxylic acid. U.S. Pat. No. 6,420,604 (Cosmoferm, NL) describes the synthesis of some ceramides by reacting sphingosine base with appropriate carbonyl halides. Particular disadvantages of this method are on the one hand the need to employ toxic organochlorine compounds, and the resulting high salt load in the final product. It is moreover obvious to a person skilled in the art that the formation of significant amounts of unwanted byproducts must be expected on use of highly reactive carbonyl halides.

Alternative synthetic routes proceed via anhydrides. Thus, for example, WO93/20038 (Gist-Brocades, NL) teaches the base-catalysed synthesis of mixed anhydrides from carboxylic acid and alkylphenylsulphonyl chloride in order to obtain reactive carboxylic acid derivatives for the N-acylation of phytosphingosine.

It is common to all these routes that they depend on the use of reactive carboxylic acid derivatives. The disadvantages in this connection are both the high corrosivity of these substances and their danger to health, making special reactor systems and precautions necessary and thus increasing the complexity of preparation. In addition, for topical applicability of the products, it must be ensured that they are freed of the reactive and toxic precursors and byproducts. High salt loads must further be expected, as well as the additional complexity associated therewith for product purification and waste disposal. A further disadvantage of the prior art processes is that only low precursor and product concentrations are obtained; thus, WO93/20038 (Gist-Brocades, NL) describes maximally 15% (w/v) precursor solutions in the toxic solvent methylene chloride with simultaneous use of reactive and toxic coreagents p-toluenesulphonyl chloride and triethylamine. In addition, either the purity of the products or the yields (in each case in the region of 80%) is unsatisfactory.

It was therefore an object of the present invention to provide an alternative way of obtaining ceramides in a harmless and industrially applicable manner, with which at least one of the prior art disadvantages can be overcome.

Amidation reactions can also be obtained biocatalytically, i.e. with use of an enzyme as catalyst. Reviews of industrial applications of enzymes are to be found for example in Liese et al. (Industrial Biotransformations; Second, Completely Revised Edition, Wiley-VCH, Weinheim, 2006). Preferred biocatalysts for synthesizing carboxylic acid derivatives are hydrolases (E.C. 3.1.x.x), especially lipases (triacylglycerol hydrolases, E.C. 3.1.1.3) and esterases (E.C. 3.1.1.1).

In accordance with their natural function in the metabolism of a cell, lipases preferentially catalyse hydrolytic cleavage of esters. However, condensative formation of esters is also described many times in the literature. Representative examples thereof are to be found in Drauz and Waldmann (Enzyme Catalysis in Organic Synthesis, A Comprehensive Handbook; Second, Completely Revised and Enlarged Edition, Vol. II, Wiley-VCH, Weinheim, 2002), in Aehle (Enzymes in Industry, Production and Applications; Second, Completely Revised Edition, Wiley-VCH, Weinheim, 2004) or in Bornscheuer (Enzymes in Lipid Modification, Wiley-VCH, Weinheim, 2000).

There are also examples in the literature of the use of amines as nucleophiles in lipase-catalysed condensation reactions.

Y.-M. Xia et al., *J Mol Catal B*, 2004, 31,111-115 describe for example the synthesis of N-lauroyl-β-aminoproprio-nitrile by amidation of methyl laurate with a reactive primary amine catalysed by a lipase from *Candida antarctica* (CALB). The disadvantages of the described process are, besides the restriction to dilute substrate solutions (below 50 mM), the comparatively lower conversion of only up to 94.3% conversion. In addition, no regio- or chemoselectivity at all is necessary in the reactions shown.

Such selectivities may, however, be absolutely necessary in the reaction according to the invention, because a precursor molecule such as, for example, phytosphingosine may possess a plurality of reactive functionalities. The problem of this selectivity is shown for example by P. Tufvesson et al.: *Biotechnol. Bioeng.*, 2007, 97(3), 447-453: in the CALB-catalysed reaction with ethanolamine with carboxylic acids, a simple selective amidation avoiding enzyme-catalysed esterification was impossible. Only by multiple addition of a precursor and removal of the water of reaction by distillation was it possible to achieve an enrichment of the desired amide.

In a further example of enzymatic amidation, M. Nechab et al.: *JOC*, 2007, 72, 6918-6923, describe the stereo-selective reaction of (R)-configured secondary amines using CALB. The high optical purity (>99% ee) of the observed products suggests a strong preference of CALB for (R)-configured amines, thus making it doubtful whether for example phytosphingosine, because of its S-configuration, reacts on the amine carbon atom with this catalyst. In addition, once again very dilute substrate solutions (100 mM) were employed, with at the same time high biocatalyst concentrations (27% w(CALB)/w(substrate)), thus significantly restricting the industrial attractiveness of the described process.

WO94/26919 (Gist-Brocades, NL) describes the enzymatic N-acylation of phytosphingosine using carboxylic esters and with use of bacterial lipases or mammalian lipases. Bacterial lipases and mammalian lipases are preferably employed in the described process; in particular a lipase from *Pseudomonas alcaligenes*. A disadvantage of this process is in particular the need for large amounts of biocatalyst (30-95% w/w) to achieve only moderate conversions (up to 78%). In addition, significant amounts of unwanted N,O-diacylation products (up to 17%) were found. Moreover only dilute solutions of the substrates were employed (59 to 93 mM), resulting in low space-time yields. A further disadvantage is the restriction to phytosphingosine base as substrate, entailing a drastic increase in the substrate costs by comparison with the use of acid addition products of phytosphingosine, for example phytosphingosine sulphate. It is moreover expressly pointed out that lipases from yeasts and fungi are unsuitable as catalysts. The process described in WO94/26919 is therefore ruled out as an economically worthwhile alternative to the existing chemical processes.

There is thus a continuing need for methods for the enzymatic amidation of lysosphingolipids which overcome the prior art disadvantages in order to make it possible to perform previously unrealizable biocatalytic synthesis of sphingolipids from alkyl carboxylates.

SUMMARY OF THE INVENTION

It was therefore an object of the present invention to provide a process which does not have one or more disadvantages of the prior art processes. In particular, the intention was to develop a process with which readily available lysosphingolipids can be employed as precursors, and moreover in high concentrations.

Further not explicitly mentioned objects are evident from the context of the following description, the examples, and the claims.

Surprisingly it was found that, contrary to the prior art, fungal lipases make the selective reaction of carboxylic esters with lysosphingolipids to form sphingolipids of high purity possible. It was additionally found that this reaction can be carried out in an economically sensible manner.

The process according to the invention and/or the biocatalyst used in accordance with the invention has the advantage that amidation reactions can be carried out in an economically worthwhile manner because either relatively low enzyme concentrations need to be employed, for example below 10% by weight based on the precursors employed, and/or the biocatalyst can be reused many times, for example at least 10 times. A further advantage of the process according to the invention is therefore products of high purity, for example with an active content of >90% and a proportion of N,O-diacetylation products below 5%, can be prepared without elaborate working-up reactions such as chromatography or fractional crystallization. A particular advantage of the process according to the invention consists in the use as carboxylic acid components of readily available alkyl carboxylates, for example methyl esters, which do not cause any unwanted secondary reactions.

DETAILED DESCRIPTION OF THE INVENTION

The present invention therefore relates to a process for the biocatalytic preparation of sphingolipids of the general formula I formula I by reacting a lysosphingolipid of the general formula II formula II with a carboxylic ester of the general formula III, formula III where $R^1$ represents a linear or branched alkyl chain which has 2 to 55 carbon atoms, optionally comprises one or more multiple bonds and/or aromatic or heteroaromatic rings, is optionally interrupted by oxygen atoms or ester or amide functionalities and is optionally substituted by at least one further group selected from alkyl, hydroxy, keto or amine groups, preferably —$CH_2$—Y—$CH_3$ where Y=a carbon-carbon bond or a linear or branched alkylene chain which has 1 to 53 carbon atoms, optionally comprises one or more multiple bonds and/or aromatic or heteroaromatic rings, is optionally interrupted by oxygen atoms or ester or amide functionalities and is optionally substituted by at least one further group selected from alkyl, hydroxy, keto or amine groups,
$R^2$ represents H, phosphocholine, serine, ethanolamine or a sugar, preferably sugar or H, most preferably H,
X represents CH=CH, $CH_2$—$CH_2$ or $CH_2$—HCOH, preferably $CH_2$—HCOH,
$R^3$ represents a branched or unbranched alkyl radical which has 1 to 12 carbon atoms and may be substituted with at least one radical —$OR^4$,
where $R^4$ independently is identical or nonidentical radicals selected from the group comprising
H
and
—C(O)$R^1$,
characterized in that a biocatalyst used includes at least one carboxylic ester hydrolase of enzyme class E.C. 3.1.1 selected from the group comprising
carboxylic ester hydrolases of enzyme class E.C. 3.1.1 which can be isolated from an organism of the kingdom of fungi, and
carboxylic ester hydrolases of enzyme class E.C. 3.1.1 which are at least 60%, preferably at least 80%, more preferably at least 90%, particularly preferably at least 95%, 98% or 99% homologous at the amino acid level with those which can be isolated from an organism of the kingdom of fungi.

"Homology at the amino acid level" means in the context of the present invention here and hereinafter the "amino acid identity" which can be determined with the aid of known methods. In general, special computer programs with algorithms taking account of specific requirements are used. Preferred methods for determining the identity generate firstly the greatest agreement between the sequences to be compared. Computer programs for determining the identity include, but are not restricted to, the GCG program package, including GAP (Deveroy, J. et al., Nucleic Acid Research 12 (1984), page 387, Genetics Computer Group University of Wisconsin, Medicine (WI), and BLASTP, BLASTN and FASTA (Altschul, S. et al., Journal of Molecular Biology 215 (1990), pages 403-410. The BLAST program can be obtained from the National Centre For Biotechnology Information (NCBI) and from further sources (BLAST handbook, Altschul S. et al., NCBI NLM NIH Bethesda ND 22894; Altschul S. et al., above).

The person skilled in the art is aware that various computer programs are available for calculating the similarity or identity between two nucleotide or amino acid sequences. Thus, the percentage identity between two amino acid sequences can be determined for example by the Needleman and Wunsch (J. Mol. Biol. (48): 444-453 (1970)) algorithm which has been integrated into the GAP program in the GCG software package (obtainable through http://www.gcg.com), specifically either by using a Blossom 62 matrix or a PAM250 matrix, a gap weight of 16, 14, 12, 10, 8, 6, or 4 and a length weight of 1, 2, 3, 4, 5, or 6. A person skilled in the art will realize that the use of different parameters will lead to slightly different results, but that the percentage identity between two amino acid sequences will not overall be significantly different. Normally, the Blossom 62 matrix is used with application of the presettings (gap weight: 12, length weight: 1).

An identity of 60% according to the above algorithm means in connection with the present invention a 60% homology. The same applies to higher identities.

In the process according to the invention the carboxylic ester of the general formula III is particularly preferably the esters of a carboxylic acid with a radical —$R^3$ of the alcohol $R^3OH$, where the carboxylic acid is selected from the group of naturally occurring fatty acid based on natural plant or animal oils with 6-30 carbon atoms, in particular with 8-22 carbon atoms. Natural fatty acids are unbranched and consist of an even number of carbon atoms. Any double bonds have the cis configuration. Examples are: caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, linolenic acid, petroselinic acid, elaidic acid, arachic acid, behenic acid, erucic acid, gadoleic acid, eicosapentaenoic acid, docosahexaenoic acid, arachidonic acid, the ester products of which are most particularly preferred.

Furthermore, in the process according to the invention, the carboxylic ester of the general formula III is preferably the ester of a carboxylic acid with a radical —$R^3$ of the alcohol $R^3OH$, where the carboxylic acid is selected from the group of hydroxylated derivatives of a polyunsaturated fatty acid. Such fatty acids are for example 9- or 13-hydroxyoctadecadienoic acid, 15-hydroxyeicosatetraenoic acid and the series of the so-called alpha-hydroxy acids. Likewise in this connection, the carboxylic acid is particularly preferably a polycondensation product of hydroxy-functionalized acids, for example poly-12-hydroxystearic acid or polyricinoleic acid.

Likewise in this connection, the carboxylic acid is particularly preferably a synthetic or naturally occurring carboxylic acid containing aromatic substituents, for example benzoic acid, cinnamic acid, ferulic acid, protocatechuric acid, gallic acid, vanillic acid, syringic acid, isoferulic acid, sinapic acid, caffeic acid, genitic acid, salicylic acid, salicyuric acid or nicotinic acid.

In the process according to the invention, $R^3$ is preferably an unsubstituted alkyl radical having 1 to 4 carbon atoms, preferably $R^3$ is selected from the group containing methyl, ethyl, vinyl, propyl, isopropyl, n-butyl, sec-butyl and tert-butyl radicals.

In a further embodiment of the process according to the invention, the carboxylic ester of the general formula III is a complete or partial ester of polyols with at least one acid $R^1COOH$. Preference for use as complete or partial esters of polyols is given to glycol, glyceryl, 1,2-pentanediyl, 1,3-pentanediyl, 1,2-butadiyl, 1,3-butadiyl, 1,4-butadiyl esters and also their isomers and unsaturated analogues.

The abovementioned starting materials, which determine the $R^3$ radical through the esterification of $R^1COOH$, can be present as pure substance or in admixture, and therefore the structure of the general formula III may as the case may be describe a mixture.

The process according to the invention can be used for the biocatalytic preparation of mixtures of sphingolipids of the general formula I by using mixtures of the general formula III having differing $R^1$.

The process according to the invention can similarly utilize mixtures of carboxylic esters of the general formula III having differing $R^3$.

It is also possible according to the invention to employ the acid addition products, also called acid addition salts, of the lysosphingolipids, like those resulting in the established fermentation processes for example in the case of the previously mentioned phytosphingosine, as described for example in P. Lersch, U. Schick, *Spec. Chem. Mag.*, 2003, 23(6), 30-31. The acid addition product of the lysosphingolipid which is preferably employed is the carboxylic acid carboxylate, sulphate, phosphate, nitrate, carbonate, hydroxide or halide, particularly preferably the chloride and sulphate of the lysosphingolipid.

On use of the acid addition product of the lysosphingolipid in the process according to the invention it is preferred for the lysosphingolipid to be prepared by deprotonation of the acid addition product of the lysosphingolipid before the enzymatic reaction.

The lysosphingolipid obtained in this way is also referred to hereinafter as lysosphingolipid base.

The deprotonating treatment can take place in solutions or suspensions of the acid addition product of the lysosphingolipid in conventional organic solvents. Examples of solvents which can be employed are: paraffins, monohydric or polyhydric alcohols (e.g.: methanol, ethanol, isopropanol, propanol, butanol, pentanol, hexanol, cyclohexanol, methylcyclohexanol, 2-butyl-1-octanol and the isomers thereof, ethylene glycol, glycerol, diacetone alcohol, isobutanol, etc.), ethers (diethyl ether, tert-butyl methyl ether, tetrahydrofuran, dioxane, polyethoxylates, polypropoxylates and copolymers etc.), ketones (acetone, methyl isobutyl ketone, methyl ethyl ketone, etc.), esters (triethyl citrate, tributyl citrate, isobutyl isobutyrate, isobutyl acetate, isononyl isononanoate, 2-ethylhexyl acetate, cyclohexyl acetate, 4-tert-butylcyclohexyl acetate). Toxicologically acceptable solvents such as methyl isobutyl ketone or 2-methyl-2-butanol are preferred.

The deprotonation step can be carried out at reaction temperatures at which the solvent is in the liquid state.

Preferably at reaction temperatures between −80° C. and +150° C., particularly preferably between 0° C. and 120° C., very particularly preferably between +25° C. and 100° C.

The solution of lysosphingolipid base obtained in this way can be employed as such for the enzymatic reaction, or can be previously filtered.

In a further embodiment of the present invention, the solvent of the deprotonation step can be removed by a method familiar to a person skilled in the art (e.g. removal by distillation, or precipitation/crystallization of the lysosphingolipid base with subsequent filtration). The lysosphingolipid base can optionally be isolated before the enzymatic reaction for example by precipitation or crystallization or by removing the solvent by distillation. It is preferred for a filtration step, in which the salts resulting in the deprotonating treatment are removed, to take place between the deprotonation of the acid addition product of the lysosphingolipid and biocatalytic preparation.

As an alternative, the lysosphingolipid base can be prepared by deprotonation of the acid addition product of the lysosphingolipid during the biocatalysis.

The deprotonation associated with an activation can take place by employing a base, preferably by means of an organic or inorganic base. Preferably employed as inorganic bases are inorganic hydroxides, carbonates, metal hydrides (such as, for example: lithium aluminium hydride, calcium hydride, sodium hydride and the like), ion exchange materials (such as, for example, cation or anion exchangers) and as organic bases are metal organyls (such as, for example, butyllithium), alcoholates, amines and their metal salts such as, for example, lithium diisopropylamide It has surprisingly been found that particularly high quality lysosphingolipid base which can be reacted particularly easily in the enzymatic reaction is provided in particular by those bases whose reaction with the acid addition salts does not formally produce any water. Particularly preferred bases are therefore those with which no water is liberated in their reaction. These are ones which do not liberate any water after protonation. An alkali metal alcoholate is preferably employed as base. This may be present for example in alcoholic solution. Sodium and potassium methanolate are particularly preferred. These can likewise be employed as solutions in organic solvents.

A further alternative for avoiding water of reaction and thus likewise preferred in the process according to the invention is the use of water-binding, preferably water-binding inorganic salts such as, for example, $Na_2SO_4$ for binding water produced in the reaction on use of alkali metal and/or alkaline earth metal hydroxides as base. $Na_2SO_4$ is preferably employed.

The molar ratio between acid addition product of the lysosphingolipid and base in the process is, according to the invention, in the range between 10:1 to 0.05:1, preferably between 3:1 to 0.2:1, particularly preferably between 1.4:1 and 0.6:1 and very particularly preferably the molar ratio between acid addition product of the lysosphingolipid and base is equimolar.

In a particular embodiment of the present invention, any water which is present is removed from the deprotonation mixture for preparing the lysosphingolipid base. Water-removal processes employed for this purpose are such as, for example, physical methods (e.g. distillation, membrane processes, extraction or adsorption (for example onto molecular sieves)) or else chemical methods (e.g.: reaction with metal hydrides and oxides or other reactants such as anhydrides, esters).

As already mentioned at the outset, in view of the prior art as described in WO94/26919 (Gist-Brocades) it is entirely surprising that fungal lipases can be employed as efficient biocatalyst in the process according to the invention.

As biocatalyst in the process according to the invention are in particular carboxylic ester hydrolases of enzyme class E.C. 3.1.1 which can be isolated from an organism of the kingdom fungi, and/or which are at least 60%, preferably at least 80%, more preferably at least 90%, particularly preferably at least 95%, 98% or 99% homologous at the amino acid level with those which can be isolated from an organism of the kingdom fungi, where the organism is selected from the group of genera *Aspergillus, Bipolaris, Candida, Fusarium, Geotrichum, Humicola, Microsporum, Mucor, Pichia, Thermomyces, Penicillium, Rhizopus, Rhizomucor, Microsporum, Mucor,*

Nocardia, Saccharomyces, Streptomyces, Thermomyces, Trichosporon, Zygosaccharomyces.

Exemplary representatives are, for example: *Aspergillus caesiellus, A. candidus, A. carbonarius, A. carneus, A. chevalieri, A. clavatus, A. costaricaensis, A. cretensis, A. deflectus, A. flaviceps, A. flavus, A. flocculatosus, A. fumigatus, A. glaucus, A. ibericus, A. lacticoffeatus, A. lentulus, A. neobridgeri, A. nidulans, A. niger, A. niveus, A. ochraceus, A. oryzae, A. parasiticus, A. penicilloides, A. piperis, A. pseudoelegans, A. pseudofisheri, A. restrictus, A. roseoglobulus, A. sclerotioniger, A. sojae, A. steynii, A. sydowi, A. terreus, A. udagawae, A. ustus, A. versicolor, A. westerdijkiae, Bipolaris australiensis, B. hawaiiensis, B. picifera, Candida antarctica, C. cylindracea, C. lipolytica, C. rugosa, C. utilis, C. robusta, C. kefyr, C. albicans, C. glabrata, C. krusei, C. lusitaniae, C. parapsilosis, C. tropicalis, Fusarium chlamydosporum, F. coeruleum, F. dimerum, F. incarnatum, F. moniliforme F. oxysporum, F. proliferatum, F. sacchari, F. semitectum, F. solani, F. sporotrichoides, F. sub glutinans, F. tabacinum, F. verticillioides, Geotrichum candidum, G. klebahnii, Humicola fuscoatra var. Fuscoatra, H. a grisea var. Grisea, H. grisea var. Thermoidea, H. insolens, Microsporum amazonicum, M. audouinii, M. audouinii var. Langeronii, M. audouinii var. Rivalierii, M. boullardii, M. canis, M. canis var. distortum, M. cookei, M. equinum, M. ferrugineum, M. fulvum, M. gallinae, M. gypseum, M. nanum, M. persicolor, M. praecox, M. racemosum, M. vanbreuseghemii Mucor javanicus, M. pusillus, M. plumbeus, M. racemosus, M. hiemalis, Nocardia asteroides, N. brasiliensis, N. otitidiscaviarum, Penicillium aurantiogriseum, P. brevicompactum, P. chrysogenum, P. camemberti, P. digitatum, P. citrinum, P. commune, P. corylophilum, P. crustosum, P. cyclopium, P. expansum, P. funiculosum, P. glabrum, P. glaucum, P. griseofulvum, P. italicum, P. marneffei, P. nalgiovense, P. nordicum, P. notatum, P. palitans, P. purpurrescens, P. purpurogenum, P. olsonii, P. oryzae, P. roqueforti, P. variabile, P. viridicatum, P. verrucosum, Pichia acaciae, P. amylophilia, P. ciferrii, P. pastoris, P. alni, P. americana, P. amethionina, P. angophorae, P. angusta, P. anomala, P. antillensis, P. barkeri, P. besseyi, P. bimundalis, P. bispora, P. bovis, P. cactophila, P. canadensis, P. capsulata, P. caribaea, P. castillae, P. chambardii, P. delftensis, P. deserticola, P. dryadoides, P. euphorbiae, P. euphorbiiphila, P. fabianii, P. faecalis, P. farinosa, P. fermentans, P. finlandica, P. fluxuum, P. galaeiformis, P. glucozyma, P. guilliermondii, P. hampshirensis, P. haplophila, P. heedii, P. heimii, P. henricii, P. holstii, P. inositovora, P. jadinii, P. japonica, P. kluyveri, P. kodamae, P. lynferdii, P. maganishii, P. media, P. membranifaciens, P. methanolica, P. methylivoria, P. mexicana, P. meyerae, P. minuta, P. mississippiensis, P. nakasei, P. nakazawae, P. norvegensis, P. oezlemii, P. ofunaensis, P. ohmeri, P. onychis, P. opuntiae, P. petersonii, P. philodendri, P. philogaea, P. pijperi, P. pini, P. populi, P. pseudocactophila, P. quercuum, P. rabaulensis, P. rhodanensis, P. salicaria, P. scolyti, P. segobiensis, P. silvicola, P. spartinae, P. stipitis, P. strasburgensis, P. subpelliculosa, P. sydowiorum, P. tannicola, P. thermotolerans, P. toletana, P. trehalophila, P. triangularis, P. veronae, P. wickerhamii, P. xylosa, Thermomyces lanuginosa, Rhizopus arrhizus, R. delemar, R. niveus, R. oryzae, R. azygosporus, R. microsporus, R. schipperae, R. stolonifer, Rhizomucor miehei, Saccharomyces barnettii, S. bayanus, S. castellii, S. cerevisiae, S. dairenensis, S. exiguus, S. paradoxus, S. pastorianus, S. rosinii, S. servazii, S. spencoerorum, S. transvaalensis, S. unisporus, S. bailii, Streptomyces spp., Trichosporon asahii, T. asteroides, T. beigelii, T. coremiiforme, T. cutaneum, T. faecale, T. gracile, T. inkin, T. mucoides, T. ovoides, T. pullulans, Zygosaccharomyces bisporus, Z. cidri, Z. fermantati, Z. florentinus, Z. mellis, Z. microellipsoides, Z. mrakii, Z. rouxii.*

Carboxylic ester hydrolases particularly preferably employed in the process according to the invention are enzymes selected from the group of the lipase from *Thermomyces lanuginosus* (accession number 059952), lipases A and B (accession number P41365) from *Candida antarctica* and the lipase from *Mucor miehei* (accession number P19515), the lipase from *Rhizomucor javanicus* (accession number S32492), the lipase from *Rhizopus oryzae* (accession number P61872), the lipases from *Candida rugosa* (accession number P20261, P32946, P32947, P3294 and P32949), the lipase from *Rhizopus niveus* (accession number P61871), the lipase from *Penicillium camemberti* (accession number P25234), the lipases from *Aspergillus niger* (ABG73613, ABG73614 and ABG37906) and the lipase from *Penicillium cyclopium* (accession number P61869), as well as in each case those which are at least 60%, preferably at least 80%, more preferably at least 90%, particularly preferably at least 95%, 98% or 99% homologous at the amino acid level. Concerning homology reference may be made to the abovementioned definition.

Commercial examples and likewise preferably employed carboxylic ester hydrolases in the process according to the invention are the commercial products Lipozyme TL IM, Novozym 435, Lipozyme IM 20, Lipase SP382, Lipase SP525, Lipase SP523, (all commercial products of Novozymes A/S, Bagsvaerd, Denmark), Chirazyme L2, Chirazyme L5, Chirazyme L8, Chirazyme L9 (all commercial products of Roche Molecular Biochemicals, Mannheim, Germany), and Lipase M "Amano", Lipase F-AP 15 "Amano", Lipase AY "Amano", Lipase N "Amano", Lipase R "Amano", Lipase A "Amano", Lipase D "Amano", Lipase G "Amano" (all commercial products of Amano, Japan).

The biocatalyst is preferably employed in anhydrous or partially hydrated form. It can be employed immobilized or as lyophilisate. Carriers which can be used for the immobilization are inert organic or inorganic carriers. The inert carriers preferably used or present in the immobilized form of the enzyme are those particulate carriers which have a particle size distribution in which at least 90% of the particles have a particle size of from 10 to 5000 µm, preferably from 50 µm to 2000 µm. Organic carriers which can particularly be employed are those including or consisting of polyacrylate, polymethacrylate, polyvinylstyrene, styrene-divinylbenzene copolymers, polypropylene, polyethylene, polyethylene perepthalate, PTFE and/or other polymers. It is possible to employ as carrier material, depending on the enzyme to be immobilized, in particular acidic or basic ion exchange resins, for example Duolite A568, Duolite XAD 761, Duolite XAD 1180, Duolite XAD 7HP, Amberlite IR 120, Amberlite IR 400, Amberlite CG 50, Amberlyst 15 (all products of Rohm and Haas) or Lewatit CNP 105 and Lewatit VP OC 1600 (products of Lanxess, Leverkusen, Germany). Inorganic carriers which can be employed are oxidic and/or ceramic carriers known in the state of the art. The inorganic carriers which can be employed in particular are for example Celite, zeolites, silica, controlled-pore glass (CPG) or other carriers like those described for example in L. Cao, "Carrier-bound Immobilized Enzymes: Principles, Application and Design", Wiley-VCH: 2005, Weinheim, Germany. The inert carriers present in the immobilized form of the enzyme or the inert carriers used to produce the immobilized forms of the enzyme particularly preferably consist of polyvinylstyrene, polymethacrylate or polyacrylate.

Immobilization on the particles is possible according to the invention covalently or noncovalently, preferably noncovalently. For noncovalent immobilization, the carrier can be incubated or impregnated for example with an aqueous enzyme solution which may optionally comprise further constituents such as, for example, inorganic salts or detergents. This incubation/impregnation can be carried out for example at temperatures between 0° C. and 50° C., preferably between 0° C. and 40° C. The incubation/impregnation preferably takes place over a period of from a few minutes up to some hours. The progress of the incubation can be followed by determining the concentration of the enzyme in the solution by conventional methods for protein determination. After the desired degree of immobilization has been reached, the carrier can preferably be washed with water and, if desired, dried.

It is also possible to use whole cells which comprise a suitable biocatalyst, either as resting cells or in dried form, preferably permeabilized by a prior art method.

The biocatalyst can be used according to the invention in a quantitative ratio to the substrates employed of from 0.01% (w/w) to 300% (w/w). The preferred mass ratio follows from the specific activity of the biocatalyst under the respective reaction conditions (especially depending on the substrates, the concentration thereof, the solvent and the reaction temperature). Depending on these parameters, a preferred amount of biocatalyst is one making complete conversion of the reactants possible within a period of from 1 to 96 hours, preferably from 8 to 24 hours. The amount of biocatalyst, based on the total mass of precursors, is preferably employed in a range between 1% (w/w) and 100% (w/w) and very particularly preferably between 1% (w/w) and 50% (w/w), in particular between 1% (w/w) and 20% (w/w).

In a particular embodiment, the biocatalyst is recovered.

It is possible according to the invention for the reactants to be present at the start of the enzymatic reaction in a molar ratio of lysosphingolipid to carboxylic ester of from 1:10 to 10:1. The term "molar ratio" relates in this connection to the molar ratio of lysosphingolipid amines to acyl donor carboxylate groups. Ratios of amounts between 1:3 and 3:1 are preferably employed. Ratios of amounts between 1:1.4 and 1.4:1 are particularly preferably employed, especially equimolar ratios of amounts.

The reactants can either be present in the molten state without further solubilizers or be dissolved or suspended in an organic solvent. The reaction is preferably carried out in the organic solvent. Particularly suitable solvents are those able to dissolve the reactants in high concentrations at temperatures in the range from 20° C. to 130° C. Examples which have proved to be particularly suitable, without any restriction to these solvents, are ketones such as, for example, methyl isobutyl ketone or cyclohexanone, sterically hindered secondary alcohols such as 2-butyl-1-octanol, methylcyclohexanols, 1-methoxy-2-propanol, 2,3-butanediol 2-octanol, diacetone alcohol, 2-methyl-2-butanol, sterically hindered esters such as 4-tert-butylcyclohexyl acetate, 2-ethylhexyl acetate, cyclohexyl acetate and ethers such as 1,4-dioxane, tetrahydrofuran and Varonic APM (Evonik Goldschmidt GmbH, Essen, Germany). Solvents which have proved to be unsuitable are those, especially esters, which are converted with significant activity by the biocatalyst. In the reaction with phytosphingosine as precursor and use of ethyl butyrate it was possible for example to detect besides the desired product significant amounts of N-butyrylphytosphingosine and transesterification product with the acyl donor employed (e.g. methyl stearate). The same applies to the use of butyl acetate (formation of N-acetylphytosphingosine and acyl donor butyl ester).

The reaction is preferably carried out under anhydrous conditions, defined as a water content not exceeding 0.100 M, preferably not exceeding 0.010 M and particularly preferably at a maximum of 0.005 M, detected by the Karl Fischer method.

High substrate concentrations are particularly advantageous for the reaction rate. High product concentrations result therefrom when the conversions are high, but surprisingly do not have negative effects on the enzyme activity when the conversions are high. This is surprising to a person skilled in the art since product inhibition is normally observed in enzymatic reactions. In addition, it has surprisingly been found that removing one of the reaction products (ceramide or alcohol) from the reaction mixture is not absolutely necessary to achieve very high to quantitative conversions. According to Le Chatelier's principle, which is familiar to a person skilled in the art, this would have been expected with the present equilibrium reaction. The prior art (WO94/26919, Gist-Brocades) reaction conversions of only 67% to 78% led to the expectation of the necessity thereof. However, it is possible according to the invention to react even lower substrate concentrations efficiently.

A reactant concentration at the start of the reaction which is preferred in the context of the invention is in the range between 0.01 M and 3 M, in particular in the range between 0.2 M and 2 M and particularly preferably in the range between 0.5 M and 1.5 M for each reactant.

Concerning the reaction temperature, it has been found that temperatures which are particularly suitable are those at which the substrates are homogeneously soluble in the solvent. Reaction temperatures in the range between 20° C. and 130° C. have proved to be advantageous in this connection. Especially at high temperatures, careful degassing of the reaction mixture is needed because of colour changes. However, it has surprisingly been found that precautions of this type are unnecessary at reaction temperature of 100° C. and below. The reaction temperatures are therefore preferably in the range from 40° C. to 90° C. and very particularly preferably in the range between 70° C. and 85° C.

The reaction is preferably carried out under a pressure of less than 1 bar, preferably less than 0.5 bar and particularly preferably less than 0.05 bar.

The reaction can be carried out in a batch process (stirred vessel) or in a fixed bed reactor continuously or semicontinuously. A high rate of inactivation of the biocatalyst was to be assumed especially in the batch process. Mention should be made here of the mechanical destruction of the biocatalyst owing to the mechanical stress occurring through stirring, and thermal inactivation of the biocatalyst paired with inactivating effects caused by reactants and solvents. Such effects are known to a person skilled in the art and appropriate remedies are disclosed in the literature. It is thus possible for example if mechanical attrition of the biocatalyst occurs in a stirred process to avoid this by employing a fixed bed. Further reactor types as are known to a person skilled in the art are likewise suitable for avoiding mechanical enzyme inactivation.

It is further to be expected on use of esters as acyl donors that the biocatalyst will be chemically inactivated by the liberated alcohols (e.g.: Y. Yoshida et al., J. Biosci. Bioeng., 2006, 102(1), 66-68). Methods for avoiding such inactivations are known to a person skilled in the art and include for example removal of the alcohol by distillation from the reaction mixture or use of membrane processes. However, it has surprisingly been found that even without use of the processes described above it is possible to reuse the biocatalyst many times without significant loss of activity.

It is common to all the processes described in the prior art that the resulting products are compositions of sphingolipid and high proportions (up to 19% of the total product) of the corresponding N,O-diacylation product. These compositions are entirely unemployable in cosmetic compositions for example because the proportion of N,O-diacylation product is not less than 5%. It has surprisingly further been found that in the process according to the invention amidation of the secondary amine function is distinctly preferred over esterification of one of the alcohol functions. A contrary behaviour, in particular a preference for the primary, that is to say sterically easily accessible, alcohol function would have been expected. The prior art (WO94/26919, Gist-Brocades) describes a similar situation: the reaction products obtained therein contained significant proportions of N,O-diacylation product (mono- to diacylation product>1:5) on use of a bacterial lipase and even with a 60% molar excess of the acyl donor over phytosphingosine.

By contrast, it was possible to show in the process according to the invention that even with a 3.6-fold excess of acyl donor over lysosphingolipid there is no significant diacylation as long as lysosphingolipid is still present in the reaction mixture. Only after the lysosphingolipid has been completely converted to sphingolipid was it possible to detect slow esterification activity. On stoichiometric use of lysosphingolipid and acyl donor, the unwanted side reaction described above was scarcely observed.

The present invention therefore relates to a process with which particularly pure N-acylphytosphingosines are obtained even as crude products from the enzymatic reaction. The conversion in relation to the target compound according to formula I is preferably more than 80%, particularly preferably more than 85% and very particularly preferably more than 90% of the conversion to be expected theoretically.

The process according to the invention is further suitable for preparing a composition comprising formula I and from 0.001 to 19% by mass, preferably 0.005 to 19% by mass, particularly preferably 0.01 to 5% by mass, of the corresponding N,O-diacetylation product.

The invention thus likewise relates to compositions comprising formula I and from 0.001 to 19% by mass, preferably 0.005 to 19% by mass, particularly preferably 0.01 to 5% by mass, of the corresponding N,O-diacetylation product, prepared using the process according to the invention.

The invention likewise relates to the sphingolipid prepared using the process according to the invention.

The present invention further relates to a method for isolating the sphingolipid from the reaction mixture. Owing to its advantageous physical properties, the sphingolipid can easily be removed from the reaction solution by crystallization/precipitation and thus purity of the crude product, which is already high, can be increased further in a simple manner.

Sphingolipids and compositions according to the invention are particularly suitable for producing cosmetic and pharmaceutical formulations. The invention likewise therefore relates to cosmetic or pharmaceutical formulations comprising at least one sphingolipid according to the invention and/or one composition according to the invention.

The present invention is described by way of example in the examples detailed below, without the invention, whose range of application is evident from the complete description and the claims, being intended to be restricted to the embodiments mentioned in the examples.

Figure 1:
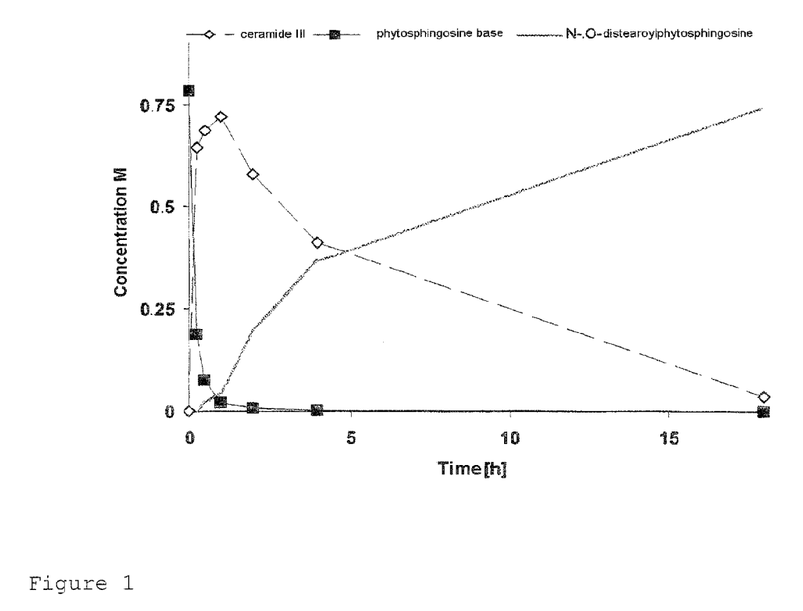
FIG. 1 is graph illustrating the course of an enzymatic reaction phytosphingosi with a 3.4-fold excess of acyl donor.

The following figures are part of the examples:

FIG. 1: course of an enzymatic reaction of phytosphingosi with a 3.4-fold excess of acyl donor.

Figure 2:
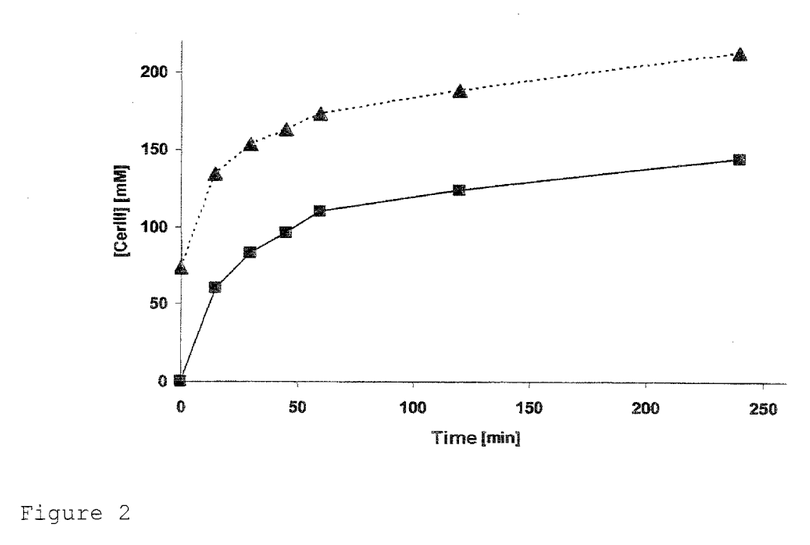
FIG. 2 is a graph comparing the course of an enzymatic reaction of phytosphingosines with methyl sterate; wherein the triangles denote additional N-stearoylphytosphingosine, and the squares denote no additional N-stearoylphytosphingosine.

FIG. 2: comparison of course of enzymatic reaction of phytosphingosines with methyl stearate. Triangles: with additional N-stearoylphytosphingosine, squares: no additional N-stearoylphytosphingosine.

Figure 3:
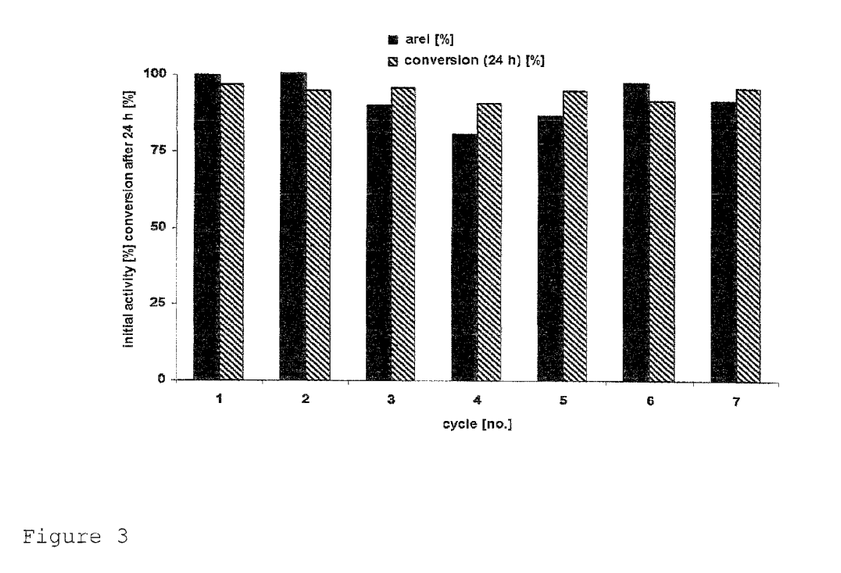
FIG. 3 is a plot showing the recycling of biocatalyst: the initial activities of the cycles concerned are reproduced in black and the yields after 24 h are reproduced hatched.

FIG. 3: recycling of biocatalyst: the initial activities of the cycles concerned are reproduced in black and the yields after 24 h are reproduced hatched.

Figure 4:
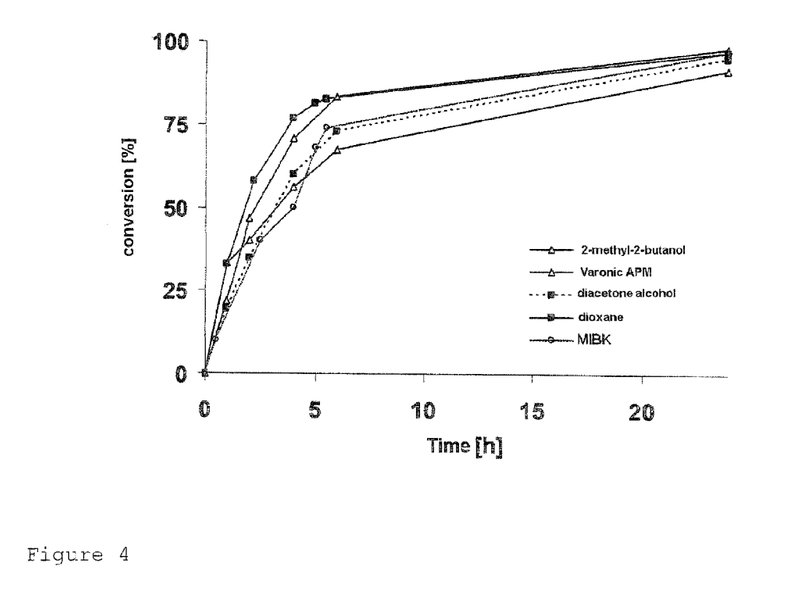
FIG. 4 is a graph illustrating time-conversion curves of an enzymatic reaction of phytosphingosine with methyl stearate in various solvents.

FIG. 4: time-conversion curves of enzymatic reaction of phytosphingosine with methyl stearate in various solvents.

Figure 5:
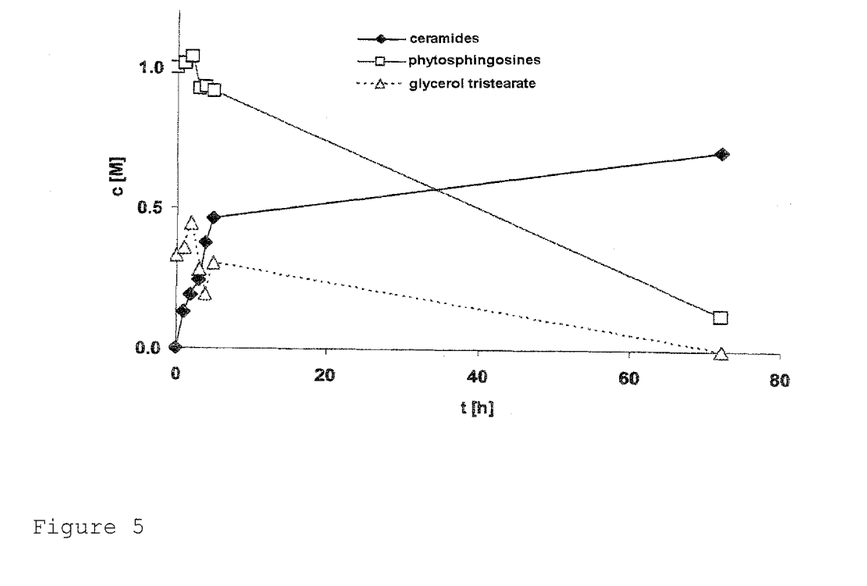
FIG. 5 is a graph illustrating the course of an enzymatic ceramide III synthesis using tristearin as acyl donor.

FIG. 5: course of an enzymatic ceramideIII synthesis using tristearin as acyl donor.

EXAMPLES

Example 1

Deprotonation of PS Sulphate 100 g of phytosphingosine sulphate (Cosmoferm, Delft, NL) are suspended in 600 g of methanol at 55° C., admixed with 46 g of sodium methoxide and stirred at 55° C. for 150 minutes. Then, the suspension is filtered hot and the filtrate is concentrated. The pale beige solid (78 g) is used for further experiments.

Example 2

Screening of Commercial Lipases for Amidation Reactivity

In an equimolar solution of phytosphingosine (from Example 1) and methyl stearate (each 1M) in dioxane (11 mL), 0.35 g (5% w/w) each of the fungal lipases listed in Table 1 are suspended and shaken for 72 h at 80° C. lipase. Then, the biocatalyst is filtered off hot and the filtrate is analysed by gas chromatography.

TABLE 1 investigation of various yeast or fungal lipases for suitability as N-acylation catalyst for phytosphingosine.

| Lipase from | % ceramide | % phytosphingosine | % methyl stearate |
|---|---|---|---|
| Rhizomucor miehei | 15.0 | 10.9 | 6.8 |
| Thermomyces lanuginosa | 7.1 | 17.3 | 12.9 |
| Candida rugosa | 3.6 | 16.8 | 17.7 |
| Candida cylindracea | 3.2 | 14.6 | 15.7 |
| Candida antarctica (Lipase A) | 2.9 | 20.2 | 15.6 |
| Candida antarctica (Lipase B) | 23.1 | 5.3 | 4.4 |

Lipase B from *Candida antarctica* was used for further experiments.

Example 4

Negative Control

To exclude any possible uncatalysed reaction of phytosphingosine with the acyl donor, phytosphingosine was dissolved in methyl stearate in 0.2 M strength at 80° C. and incubated for 4 h. The subsequent analysis by gas chromatography did not show any significant (quantifiable) conversion.

Example 5

Reactions with Phytosphingosine Sulphate

To demonstrate the need to deprotonate phytosphingosine sulphate, the following comparative experiment was carried out: 8.18 g of phytosphingosine sulphate and 6.72 g of methyl stearate were suspended in 15 mL of dioxane 80° C. and admixed with 0.16 g of Novozym 435. After 4 hours' incubation with stirring, the reaction mixture was analysed by gas chromatography. Only 31.7 mM of N-stearoylphytosphingosine were found. In a comparative experiment under identical conditions but after addition of 2.4 g of sodium carbonate, 368 mM N-stearoylphyto-sphingosine were found.

Example 6

Regioselectivity of Enzymatic Acylation

To obtain a high excess of acyl donor relative to phytosphingosine, 4.43 g of phytosphingosine were dissolved in 15.09 g of methyl stearate at 120° C. This solution was admixed with 0.98 g of Novozym 435 (5% w/w) and stirred under standard pressure. Periodically, samples were taken and analysed by gas chromatography.

As is discernible from the reaction course (FIG. 1), significant accumulation of the unwanted N,O-distearylphytosphingosine only takes place at complete conversion of the phytosphingosine used. After an hour, at a residual phytosphingosine concentration of 19 mM (conversion>99.5%) no N,O-diacylation product is as yet detectable; formation of the N,O-diacylation product is only observed at below a phytosphingosine concentration of about 5 mM. In addition, the reaction rate of the secondary reaction is below that of the desired reaction by a factor of more than 25.

Example 7

Experiment Concerning Product Inhibition

To exclude any product inhibition, 2 concurrent experiments were carried out. To this end, 1.59 g of phytosphingosine in each case were dissolved with 7.45 g of methyl stearate in 25 mL of dioxane at 80° C. and admixed with 0.49 g of Novozyme 435 in each case. One of the two reaction mixtures was additionally admixed with 1.3 g of N-stearoylphytosphingosine (Cosmoferm, Delft, NL). As the comparison of the two time-conversion curves shows (FIG. 2), the reaction trajectories are identical, and so it is possible to exclude any pronounced product inhibition.

Example 8

Reusability of Biocatalyst

To evaluate the reusability of the biocatalyst, a series of experiments was conducted as follows: 3.3 g of phytosphingosine were dissolved together with 14.9 g of methyl stearate in 50 mL of dioxane at 80° C. and the reaction was started by addition of 0.98 g of Novo435. Samples were periodically taken and analysed by gas chromatography and the initial rate and conversion were calculated therefrom. After 24 h, the reaction batch is filtered hot and the enzyme remaining behind is washed three times with 50 ml of hot (50° C.) dioxane each time. Then, the biocatalyst thus recycled is re-used under the same conditions as described above. This procedure is repeated altogether six times.

As is clear from FIG. 3, the biocatalyst can be used for the reaction at least seven times without any observable decrease in activity.

Example 9

Determination of Kinetic Parameters of Biocatalyst

The kinetic parameters of the enzymatic N-acylation were determined as follows: the concentration of one reactant was varied while the concentration in the other was kept constant. The reactions were carried out in dioxane at 80° C. using the same amount of enzyme in each case. Samples were periodically taken and analysed by gas chromatography; from that, the respective initial rates were determined and analysed according to Lineweaver-Burk. The results determined were a $K_M$ value of 400 mM for phytosphingosine and a $K_M$ value of 196 mM for methyl stearate.

Example 10

Influence of Temperature on Reaction Rate

Enzymatic reactions were carried out at various the substrates were used in equimolar amounts in all cases. The enzyme quantity used was 1.4% (w/w) in each case. The results of the gas-chromatographic evaluation of the initial rate and also of the conversion after 4 hours are reproduced in Table 2.

TABLE 2

Influence of reaction temperature on enzymatic synthesis of N-stearoylphytosphingosine.

| T [° C.] | Initial concentration [M]/solvent | Aspec [Ug-1] | conversion after 4 h [%] |
|---|---|---|---|
| 80 | 0.98 (in dioxane) | 840 | 49.5 |
| 100 | 2.8 (none) | 1182 | 79 |
| 120 | 2.8 (none) | 1224 | 92 |

Example 11

Using Various Solvents

Phytosphingosine and methyl stearate were each dissolved at 1M in the respective solvent at 80° C., admixed with 5% (w/w) of Novozym 435 and stirred. Periodically samples were taken and analysed by gas chromatography. As is apparent from FIG. 4, the conversion-time curves and also the conversions after 24 h of the individual reactions are almost coincident.

Example 12

Enzymatic Reaction of Phytosphingosine with Various Fatty Acid Esters

Phytosphingosine and the acyl donors reported in Table 3 were each dissolved at 1M in the solvent at 80° C., admixed with 5% (w/w) of Novozym 435 and stirred. Periodically samples were taken and analysed by gas chromatography.

TABLE 3

Results of enzymatic reaction of various acyl esters with phytosphingosine.

| Substrate | Conversion in % (reaction time, solvent) |
|---|---|
| Ethyl hexanoate | 98.2 (24 h, MIBK) |
| Methyl oleate | 97.4 (23 h, tert-butanol) |
| Methyl ricinoleate | 96.5 (24 h, tert-butanol) |
| Ethyl o-salicylate | 36.5 (24 h, MIBK) |

Example 13

Selective Crystallization of Product

Methyl stearate (734 mM) and phytosphingosine (146 mM) were dissolved in 2-methyl-2-butanol at 80° C., admixed with 5% (w/w) of Novozym 435 and stirred at 80° C. for 20 h. Then, the enzyme was filtered off hot and the clear starting solution was temperature conditioned at 45° C. overnight. The precipitated solid was filtered off, and filtrate and filter residue were analysed by gas chromatography. As is evident from Table 4, fractional precipitation makes it possible to achieve selective enrichment of the desired product even in the presence of high substrate excesses.

TABLE 4

Results of selective precipitation of reaction product from a reaction mixture (data: GC area percent).

|  | Methyl stearate | Phytosphingosine base | CerIII |
|---|---|---|---|
| Starting solution | 69.3 | 0.14 | 30.5 |
| Filtrate | 90.1 | 0.1 | 9.8 |
| Precipitate | 5.0 | 0.08 | 94.9 |

Example 14

Tristearin as Acyl Donor

Enzymatic reactions were carried out using triglyceride (tristearin) as acyl donor. 0.5 g of Novozym 435 was added to a solution of 5.4 g of phytosphingosine and 5 g of tristearin in 17 g of dioxane at 80° C. and stirred under atmospheric pressure. Samples were taken periodically and analysed by gas chromatography.

As is clear from FIG. 5, complete conversion of the acyl donor is possible. It surprisingly emerged from the analysis by gas chromatography that no significant amounts of intermediate partial glycerides (glycerol distearate or glycerol monostearate) were observable.

Example 15

One-pot Synthesis of N-stearoylphytosphingosine from Phytosphingosine Sulphate 100 g of phytosphingosine sulphate (Cosmoferm, Delft, NL) are suspended in 100 ml of MIBK (methyl isobutyl ketone) at 55° C., admixed with 46 g of sodium methoxide and stirred at 55° C. for 180 minutes. Then, 73.3 g of methyl stearate and 5 g of Novo435 are added. The suspension thus obtained is stirred at 80° C. for 36 hours and filtered off hot. The clear filtrate is left to stand at room temperature for 4 hours and the precipitated clear beige solid (122.3 g of N-stearoylphytosphingosine, purity >97%) is filtered off.

Example 16

Pilot Batch in Fixed-bed Reactor 207.8 g of phytosphingosine sulphate are suspended in 500 ml of MIBK at 55° C. together with 108.04 g of $NaOCH_3$ solution (25% strength in methanol) and subsequently transferred hot via a filter press into a fixed-bed reactor and admixed with 149.3 g of methyl stearate. The fixed bed contains 17.8 g of Novozyme 435. The entire reactor is thermostated to 80° C. The fixed bed is flushed with the reaction mixture at a pumping rate of about 25 ml $min^{-1}$. An underpressure of 0.8 bar is applied to remove excess methanol. After 24 h, the reactor is vented with nitrogen, emptied and the reaction solution is left to stand at room temperature overnight. The precipitated solid is filtered off (287.1 g of N-stearoylphytosphingosine, purity 98.7%).

The invention claimed is:

1. A process for the biocatalytic preparation of a sphingolipid of formula I formula I comprising:
preparing a lysosphingolipid of formula II formula II by deprotonation of an acid addition product of said lysosphingolipid, wherein said deprotonation employs a base that does not liberate any water during said deprotonation; and reacting said lysosphingolipid with a carboxylic ester of formula III formula III where $R^1$ represents a linear or branched alkyl chain which has 2 to 55 carbon atoms,
$R^2$ represents H, phosphocholine, ethanolamine, serine or a sugar,
X represents CH=CH, $CH_2$—$CH_2$ or CHOH,
$R^3$ represents a branched or unbranched alkyl radical with has 1 to 12 carbon atoms and may be substituted with at least one radical —$OR^4$, where $R^4$ is selected from the group consisting of H and —C(O)$R^1$, where $R^1$ is a defined above, in the presence of a biocatalyst that comprises at least one carboxylic ester hydrolase of enzyme class E.C. 3.1.1 which is/are at least 80% homologous at the amino acid level with a carboxylic ester hydrolase of enzyme class E.C. 3.1.1 isolated from an organism of the kingdom of fungi.

2. The process according to claim 1, wherein $R^3$ is an unsubstituted alkyl radical having 1 to 4 carbon atoms.

3. The process according to claim 1, wherein the lysosphingolipid is prepared before said reacting said lysosphingolipid with said carboxylic ester.

4. The process according to claim 3, wherein a filtration step takes place between the deprotonation of the acid addition product of the lysosphingolipid and said reacting said lysosphingolipid with said carboxylic ester.

5. The process according to claim 3, wherein the acid addition product of the lysosphingolipid comprises a carboxylic acid carboxylate, sulphate, phosphate, nitrate, carbonate, hydroxide or halide of the lysosphingolipid.

6. The process according to claim 1, wherein the lysosphingolipid is prepared during said reacting said lysosphingolipid with said carboxylic ester.

7. The process according to claim 1, wherein said base is an alkali metal alcoholate.

8. The process according to claim 1, wherein a molar ratio between acid addition product of the lysosphingolipid and said base is in a range between 10:1 to 0.05:1.

9. The process according to claim 1, wherein the organism of the kingdom of fungi is selected from the group of genera *Aspergillus, Bipolaris, Candida, Fusarium, Geotrichum, Humicola, Microsporum, Mucor, Pichia, Thermomyces, Penicillium, Rhizopus, Rhizomucor, Microsporum, Mucor, Nocardia, Saccharomyces, Streptomyces, Trichosporon,* and *Zygosaccharomyces*.

10. The process according to claim 1 wherein the biocatalyst is present in an amount, based on the total mass of the compounds of formula I and of formula II, between 1% (w/w) and 100% (w/w).

11. The process according to claim 1, further comprising recovering said biocatalyst.

12. The process according to claim 1, wherein a molar ratio of lysosphingolipid to carboxylic ester at a start of said reacting said lysosphingolipid with said carboxylic ester is from 1:10 to 10:1.

13. The process according to claim 1, wherein the reacting said lysosphingolipid with said carboxylic ester is carried out in an organic solvent.

14. The process according to claim 1, wherein the reacting said lysosphingolipid with said carboxylic ester is carried out under anhydrous conditions, defined as a water content not exceeding 0.1 M detected by the Karl Fischer method.

15. The process according to claim 1, wherein each of said lysosphingolipid and said carboxylic ester is present at the start of the reaction in the range between 0.01 M to 3 M.

16. The process according to claim 1, wherein said reacting said lysosphingolipid with said carboxylic ester is performed at a reaction temperature in a range between 20° C. and 130° C.

17. According claim 1 wherein said reacting said lysosphingolipid with said carboxylic ester is performed at a pressure of less than 1 bar.

18. The process according to claim 1, wherein conversion of a compound according to formula II to a compound of formula I is more than 80% of the conversion to be expected theoretically.

19. The process according to claim 1, wherein a composition comprising formula I and from 0.001 to 19% by mass of the corresponding N,O-diacetylation product is obtained.

* * * * *